United States Patent [19]
Pierce et al.

[11] Patent Number: 6,063,369
[45] Date of Patent: May 16, 2000

[54] QUATERNIZED HEMP SEED OIL

[75] Inventors: Deborah Pierce, Walnut, Calif.; Geoffrey Brooks, Warren, N.J.

[73] Assignee: Alterna, Inc., Los Angeles, Calif.

[21] Appl. No.: 09/040,269

[22] Filed: Mar. 16, 1998

[51] Int. Cl.[7] ..................................................... A61K 7/08
[52] U.S. Cl. ...................... 424/70.28; 424/70.1; 424/74; 424/195.1; 424/401
[58] Field of Search ................................ 424/70.28, 70.1, 424/74, 195.1, 401

[56] References Cited

U.S. PATENT DOCUMENTS

| | | |
|---|---|---|
| 3,986,825 | 10/1976 | Sokol . |
| 4,165,369 | 8/1979 | Watanabe et al. . |
| 4,187,289 | 2/1980 | Eckhardt . |
| 4,234,509 | 11/1980 | Billenstein et al. . |
| 4,448,708 | 5/1984 | Killat et al. . |
| 4,511,555 | 4/1985 | Faust . |
| 4,540,507 | 9/1985 | Grollier . |
| 4,548,810 | 10/1985 | Zofchak . |
| 4,837,012 | 6/1989 | Kiffel et al. . |
| 4,913,829 | 4/1990 | Rutzen et al. . |
| 4,997,912 | 3/1991 | Wirtz et al. . |
| 5,196,189 | 3/1993 | Jacquet et al. . |
| 5,344,643 | 9/1994 | Thiel et al. . |
| 5,658,954 | 8/1997 | Targosz . |
| 5,827,510 | 10/1998 | Mesquitta . |

FOREIGN PATENT DOCUMENTS

95/31176  11/1995  WIPO .

OTHER PUBLICATIONS

Bailey, "Fat Splitting," in: *Industial Oil and Products*, Chapter XIX, pp. 796–806.

Brooks, G.J., The "Essential Fatty Acid" Story and New Ideas for Their Application, *Cosmetics and Toiletries* 99:45–52 (1984).

*Primary Examiner*—Thurman K. Page
*Assistant Examiner*—Brian K. Seidleck
*Attorney, Agent, or Firm*—Klarquist Sparkman Campbell Leigh & Whinston, LLP

[57] ABSTRACT

Quaternized hemp seed oil is incorporated into cosmetic compositions, such as shampoos, hair conditioners, hair sprays, mousses, gel or sculpting lotions, pomades, and skin creams and lotions. The hemp seed oil is saponified and quaternized under gentle conditions, and in the substantial absence of oxygen, to avoid oxidation and cross-linking of essential fatty acids that provide biological benefit to the hair and skin. In a disclosed embodiment, saponification occurs in the presence of an alkali hydroxide catalyst, under a blanket of nitrogen gas at subatmospheric pressures. Subsequent quaternization is performed with a tertiary amine of the formula

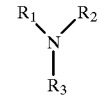

wherein $R_1$ and $R_2$ are each lower alkyl, and $R_3$ is aliphatic alkyl having 8 to 22 carbons. In a specific embodiment, the quaternizing agent is dimethylcetylamine. When incorporated into skin and hair care compositions, the resulting product exhibits surprising shine and conditioning properties, and provides essential fatty acids for biological maintenance and repair of skin and hair.

16 Claims, No Drawings

6,063,369

QUATERNIZED HEMP SEED OIL

FIELD OF THE INVENTION

This invention concerns hair and skin care products, and is more particularly directed to a method of preparing such products to improve their restorative and cosmetic properties.

BACKGROUND OF THE INVENTION

Essential fatty acids have been recognized as important biological precursors from which all human body fats, biological membranes, and prostaglandins are synthesized. Omega-6 linoleic acid (cis $\Delta^{9,12}$) and omega-3 linolenic acid (cis $\Delta^{9,12,15}$) are two unsaturated fatty acids that have been recognized as essential. They are "essential" because mammals lack the enzymes necessary to synthesize them, and they must therefore be exogenously supplied, usually in the diet. In view of their widespread biological importance, they have in the past been used as ingredients in cosmetics, such as shampoos and conditioners. Although their beneficial effects have been recognized in the past, the widespread use of these and other fatty acids in hair and skin preparations has been limited by the instability of the fatty acids, and their propensity to undergo oxidation, degradation, and become rancid. Such reactions can impair or eliminate the desired biological effects of the fatty acids.

Hempseed oil is a natural oil that can be obtained by cold pressing hemp seeds, which are seeds from the plant species *Cannabis sativa*. The oil from these seeds contains a mixture of natural fats (triesters of glycerol, also known as triglycerides). In particular, the hemp seed oil is a triester of the formula

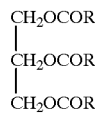

in which about 95% of the molecular weight of the molecule is the R groups, which are fatty acids selected from the group consisting of palmitic acid, stearic acid, arachidic acid, behenic acid, palmitoleic acid, oleic acid, linoleic acid and linolenic acid. This rich mixture of fatty acids includes several especially biologically important fatty acids, such as omega-6-linoleic acid (a polyunsaturated essential fatty acid), omega-6 linolenic acid, and omega-3 linolenic acid (a polyunsaturated essential fatty acid).

The particular chemical composition of some samples of hemp seed oil has been found to have a fatty acid content of approximately the following amounts:

| | | |
|---|---|---|
| palmitic acid | 5.8% | saturated |
| stearic acid | 2.6% | saturated |
| arachidic acid | 0.8% | saturated |
| behenic acid | 0.3% | saturated |
| palmitoleic acid | 0.2% | monounsaturated |
| oleic acid | 11.4% | monounsaturated |
| linoleic acid | 54.7% | polyunsaturated, omega-6 |
| linolenic acid | 2.6% | polyunsaturated, omega-6 |
| linolenic adid | 18.4% | polyunsaturated, omega-3 |

Hempseed oil has an iodine value (measure of saturation) of 166, and a very low freezing point (−20° C.) because of its high essential fatty acid content. Given the high content of essential fatty acids in hemp seed oil, attempts have been made to use hemp as an herbal treatment.

Hemp seed oil products have been commercially available in recent years, but they have been less than optimal for application to hair and skin. The oils have not been substantive enough or of long term value, and they only temporarily smooth or soften the hair or skin to which they are applied. The oils can also make the hair appear greasy, produce an adverse aesthetic feel, and are easily washed out of the hair, thereby diminishing any long term effect.

U.S. Pat. No. 4,511,555 disclosed the use of an herb, such as an extract of Indian hemp leaves, for controlling dandruff. The leaves were heated in vegetable oil for 3–5 hours at a temperature of 100–190° F., to produce the extract, which was blended into petroleum jelly and olive oil for application to the hair as a pomade. This patent does not mention the extraction of any hemp or hemp seed oils, but to the extent any oils would be present they would be polymerized, oxidized, or otherwise rendered less biologically active by the harsh extraction process.

Many cosmetic ingredients have been quaternized to impart a cationic charge to the ingredients, which helps improve their attraction or adherence to the skin and hair. Quaternization has primarily been applied to polymeric compositions, such as quaternary ammonium homopolymers and copolymers (U.S. Pat. No. 3,986,825), cationic polymers (U.S. Pat. No. 5,196,189), cationic resins and surfactants such as polysaccharides and polyamides (U.S. Pat. No. 5,344,643), vinylpyrrolidone/dialkylaminoalkyl acrylate or methacrylate copolymers (U.S. Pat. Nos. 4,540,507 and 4,837,012). Unfortunately, polymerization of biological substances often inactivates them, which makes these techniques unsuitable for use with biologically active materials, such as the essential fatty acids in hemp seed oil.

It is therefore a general object of the present invention to overcome the drawbacks of the prior art, in which processes for the quaternization of biologically active materials have rendered them substantially less active than the unquaternized form.

A specific object is to produce a substantive hair and skin care product which improves the natural benefits of hemp seed oil.

SUMMARY OF THE INVENTION

The present invention includes a method of making a cosmetic formulation containing quaternized fatty acids. More particularly, the formulation is a hemp seed oil cosmetic formulation, such as a hair or skin treatment composition, in which the fatty acids in the hemp seed oil have been quaternized without substantially oxidizing or chemically cross-linking them. The method includes at least partially hydrolyzing (for example saponifying) hemp seed oil under gentle conditions to release free fatty acids from the oil, while minimizing oxidation or cross-linking of the released fatty acids. The free fatty acids are then quaternized, again under conditions that avoid loss of biological activity of the fatty acids, particularly the essential omega-3 and omega-6 free fatty acids.

In a particular embodiment, saponification occurs at an elevated pressure, substantially in the absence of oxygen, and in the presence of a catalyst such as NaOH. Subsequent quaternization is performed by reacting the free fatty acids with a tertiary amine having the formula

wherein $R_1$ and $R_2$ are each methyl, and $R_3$ is aliphatic alkyl having 8 to 22 carbons. The tertiary amine in a disclosed embodiment is dimethylcetylamine.

In particular embodiments, saponification and quaternization can sequentially occur in a sealed reaction vessel. Saponification can be carried out under atmospheric pressure or under vacuum, but oxygen is substantially eliminated (for example less than 1% oxygen in the reaction atmosphere) to prevent oxidation of the unsaturated fatty acids. Oxygen may be evacuated from the vessel, and/or replaced with another gas that does not react with the fatty acids, such as nitrogen or argon. In the disclosed embodiment, the gas is nitrogen gas at a pressure of 30 to 40 p.s.i., for example 32 p.s.i.

The resulting quaternized free fatty acid composition is then incorporated into a cosmetic composition, such as a shampoo, hair conditioner, styling gel, and skin cream or lotion. The high content of essential free fatty acids in the composition has been found to be particularly beneficial to the skin and hair, apparently because their biological activity has not been substantially impaired by the method of preparation. The quaternization of these essential fatty acids has also been found to provide an unexpected degree of beneficial shine to hair to which it is applied. It also provides an unexpectedly superior degree of smoothing, softening, strength and moisturization to the hair, and suppleness and moisturization to the skin to which it is applied.

The present invention also includes hemp seed oil containing fatty acids that have been quaternized by this method, and cosmetic compositions (such as skin and hair care products) that incorporate the quaternized hemp seed oil. The invention also includes methods of using the compositions to improve the health and appearance of skin and hair.

The foregoing and other objects, features, and advantages of the invention will become more apparent from the following detailed description of a preferred embodiment which proceeds with reference to the accompanying drawings.

DETAILED DESCRIPTION OF SEVERAL EMBODIMENTS

The present method of making the quaternized hemp seed oil involves the saponification of the oil under gentle conditions that avoid oxidation or cross-linking of the fatty acids, followed by quaternization under similar conditions that prevent loss of the biological activity of the essential fatty acids (and other nutrients) in the oil. The conditions under which each of these steps is performed will be described in the following Examples.

Saponification

Saponification is the alkaline hydrolysis of an ester, such as the hempseed oil triglyceride. This reaction ultimately produces glycerol and fatty acids, as shown in the exemplary reaction scheme below:

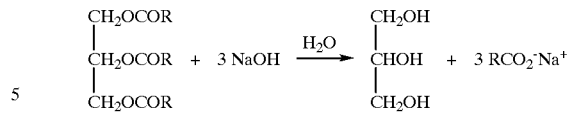

When the triglyceride is hemp seed oil, the R groups are palmitic acid, stearic acid, arachidic acid, behenic acid, palmitoleic acid, oleic acid, linolenic acid and linoleic acid, and in particular the linoleic acid may be a polyunsaturated omega-6 essential fatty acid, and the linolenic acid may be a polyunsaturated omega-6 (gamma) linoleic acid, or a polyunsaturated omega-3 linolenic essential fatty acid.

Hydrolysis of the triglyceride can be performed by any of a variety of reactions, including the Twitchell method (disclosed in U.S. Pat. No. 601,603) in which sulfonated catalysts are used. Later modifications of the Twitchell method have employed alkyl aryl sulfonic acids as catalysts in the hydrolysis reaction. However, high pressure hydrolysis is the preferred method in accordance with the present invention, to more rapidly produce fatty acids without substantial biological degradation. The catalysts used in this process can include various metallic hydroxides, of which zinc, magnesium and calcium oxides are examples. Specific examples of such catalysts include $ZnO$, $MgO$, $CaO$, $LiOH$, $NaOH$, $KOH$, or $NH_4OH$, in an amount of about 2–4%, based on the weight of the fat. A small amount of zinc dust can also be added as a reducing agent to help avoid oxidation of the fatty acids.

In prior high pressure catalytic fat hydrolysis processes, an autoclave is charged with the fat, the catalyst, and water in an amount equivalent to about 30–60% of the weight of the fat. Steam is blown through the mass to displace air in the head space and dissolved air that is released from the fat and water. The autoclave is then closed, and steam is admitted to raise the internal pressure to about 150–300 p.s.i., at a temperature of about 185–225° C. Steam is injected at the bottom of the reaction vessel to maintain agitation of the contents. Approximately 6–10 hours are required to achieve hydrolysis of 95% or more of the fat. After the desired degree of splitting is obtained, the contents are blown out into a settling tank, where the separated fatty acids are drawn off from the water-glycerol liquor.

This prior hydrolysis process was found to be unsuitable for hydrolyzing hemp seed oil for cosmetic purposes, because the fatty acids were oxidized and cross-linked by these reaction conditions, which effectively eliminated the biological activity of the fatty acids. The present invention therefore adopted a modified process in which the hydrolysis reaction is performed in the substantial absence of oxygen, for example in a vacuum or by substituting the oxygen with a blanket of an inert gas, such as nitrogen gas. This improved saponification process is illustrated in the following Example 1:

EXAMPLE 1

Saponification of Hemp Seed Oil

A 280 g amount of hempseed oil was saponified at 180° C. under a nitrogen atmosphere for 2 to 10 hours at 150 p.s.i. in a pressurized reaction vessel with agitation. The product was washed with 200 g of deoxygenated water (from which free oxygen has been removed, yielding a 250 g product of the fatty acids, 30 g of glycerin, and 200 g of water.

Quaternization of the Saponified Fatty Acids

Quaternization in the present process refers to the formation of a quaternary amine salt between the fatty acid and a tertiary amine, such as an amine salt of the formula:

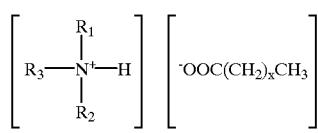

wherein $R_1$ and $R_2$ are each alkyl having 1 to 4 carbons, especially 1 to 2 carbons, for example methyl, and $R_3$ is aliphatic alkyl having 8 to 22 carbons, more specifically 12 to 18 carbons, and most particularly 16 carbons, and x is 10–20. In particular embodiments, the amine is dimethylcetylamine (C16), dimethyllaurylamine (C12), or dimethylstearylamine. Dimethylcetylamine is the preferred quaternizing agent for hair formulations, because it exhibits excellent substantitivity to the hair at low concentrations, leaves the hair with a soft feel after rinsing off, and lubricates the hair to make it easy to comb. Compared to the C12 derivative, the C16 does not foam, which allows the C16 to remain in the hair better and provides more lubrication. The C8 and C10 derivatives are also less lubricating, and do not disentangle the hair as effectively as the C16. The C18 and C22 derivatives have a heavier or waxier feel on the hair, and are not as effective at disentangling the hair. Hence the specific quaternizing agent chosen depends on the particular properties of the composition that are desired.

Generally, the dimethylcetylamine is reacted with the hempseed fatty acid and hempseed oil in roughly equal quantities, under a nitrogen atmosphere at 30–40 p.s.i. A 0.05% amount of ditertiarybutylparacresol (Ionol) and 0.25% of hypophosphurus acid may be added to retard rancidification and to maintain product color. After reaction, the mixture is cooled to about 40° C., and an alcohol (e.g. approximately 10% isopropanol) is added to reduce the viscosity of the final product and couple the unreacted free hempseed oil (under an atmosphere substantially free of oxygen) into the resultant product. The mixture is then placed under high vacuum (e.g. less than about 1 p.s.i.) for about 90 minutes to remove any volatiles.

The following specific example illustrates one particular embodiment of the quaternization reaction in accordance with the present invention.

EXAMPLE 2

Specific Example of Quaternization

Hempseed fatty acid in an amount of 250 g is mixed with 238 g dimethylcetylamine and heated under vacuum to 120° C. for 90–120 minutes, yielding 488 g dimethylcetylamine hempseedate. The hempseedate product is then mixed with 120 g of 10% isopropanol and 25 g of hempseed oil at room temperature under a nitrogen blanket to yield 633 g hempseedquat. The product is subjected to high vacuum (for example, less than 1 p.s.i.) for 30 minutes to remove any volatiles.

Formulations Incorporating the Quaternized Hemp Seed Oil

The quaternized hemp seed oil of the present invention can be incorporated into a variety of formulations, including shampoos, hair conditioners, hair styling products, fixative products (such as hair sprays, mousses and gels) that control the hair, and skin care products (such as creams and lotions). The following examples will provide detailed information and examples of each of these formulations.

EXAMPLE 3

Shampoos

A shampoo will ideally cleanse the scalp and hair without irritating the skin or eyes, while also conditioning the hair. Shampoos made in accordance with this Example are comprised mainly of water and surfactants, wherein the surfactants are anionic, nonionic, or amphoteric surfactants, or a combination of such surfactants. To offset the sometimes harsh, degreasing effects of some surfactants, ingredients such as lipids, superfatting agents, humectants and proteins can be added to shampoos. The quaternized hemp seed oil of the present invention is an example of such a soothing agent. Typical formulations incorporating the quaternized hemp seed oil of the present invention are illustrated in the following Table 1, in which percentages are by weight.

TABLE 1

| Sample Formulation for Shampoo | |
|---|---|
| Ingredient | % |
| 1. Surfactant (28%) | 25–50 |
| 2. Betaine | 3–7 |
| 3. Amide | 1–5 |
| 4. Quaternized Hemp Seed Oil | .01–10 |
| 5. Chelating Agent | 0.2 |
| 6. Water | QS |

Preservatives, perfumes and colorants as necessary.

Conditioners

Conditioners are designed to improve the condition of hair. Conventional quaternary polymers and unmodified hydrolyzed proteins may be functional conditioning agents, but are less efficient conditioners than the present invention. Quaternized hemp seed oil contains amino acids and minerals, in addition to essential fatty acids, the combination of which provides superior conditioning effects. As opposed to hemp seed oil, quaternized hemp seed oil is, by the nature of its chemistry, substantive to hair and skin, because it contains up to 24% protein by weight and 30% oil by weight. (Substantivity is the physical phenomenon by which substances that have like compositions or opposing charges to the hair and skin are readily absorbed onto or attracted to the surface of the hair or skin.)

Most conditioners are emulsions in the forms of creams, lotions and solutions, that are generally rinsed off shortly after application. "Deep conditioners" are left on the hair for longer periods of time to effectuate more intensive conditioning. This may or may not be in concert with the application of heat. "Leave in" products are left on the hair indefinitely.

TABLE 2

| Sample Formulation of a Conditioner | |
|---|---|
| Ingredient | % |
| 1. Emulsifying Wax or Equivalent Emulsifiers | 1–15 |
| 2. Fatty Alcohols | 0.5–5 |
| 3. Quaternary Ammonium Compound | 0.5–5 |
| 4. Quaternized Hemp Seed Oil | 0.01–10 |
| 5. Humectants (glycols, glycerin, etc.) | 0.5–2 |
| 6. Water | QS |

Preservatives, fragrance and color as necessary.

Styling Products

Fixatives (including hair sprays, mousses, gels, tonics, pomades) are products the primary purpose of which is to manage and control the hair, and enhance its appearance. Hair sprays may be either pump or aerosol. Mousses are typically aerosols that foam and have a low product density at the time of dispersion. Gels are thickened systems, usually clear to translucent. Hair creams and lotions are emulsion systems. Hair tonics are usually oils dissolved in alcohol. Pomades generally have a high oil content and are used for luster and to hold hair in place.

TABLE 3

Sample Formulation of a Hair Spray

| Ingredient | % |
|---|---|
| 1. SDA 40 Alcohol | QS |
| 2. Fixative Polymer | 1–20 |
| 3. Quaternized Hemp Seed Oil | 0.01–5 |
| 4. Neutralizer (AMP, TEA or NaOH) | 0.05–3 |
| 5. Fragrance | 0.25–.1 |
| 6. If aerosol, propellant to meet VOC requirement compliance | |

TABLE 4

Sample Formulation of a Mousse

| Ingredient | % |
|---|---|
| 1. Water | QS |
| 2. SD Alcohol 40 | 0–50 |
| 3. Humectants | 0.1–10 |
| 4. Fixative Polymer | 0–12 |
| 5. Quaternized Hemp Seed Oil | 0.01–10 |

Preservatives, fragrance and color as necessary.

TABLE 5

Sample Formulation of a Gel/Sculpting Lotion

| Ingredient | % |
|---|---|
| 1. Water | QS |
| 2. Fixative Polymer | .3–15 |
| 3. SD Alcohol 40 | 0–50 |
| 4. Quaternized Hemp Seed Oil | .01–10 |
| 5. Thickener (Acrylic, gums/celluloses) | .2–7 |
| 6. Humectants | .1–5 |

Preservatives, fragrance and color as necessary.

TABLE 6

Sample Formulation of Styling Lotion/Cream/Pomades

| Ingredient | % |
|---|---|
| 1. Water | QS |
| 2. Thickener/Stabilizer | 0.1–1.0 |
| 3. Humectant | 1–5 |
| 4. Emulsifiers | 0.5–15 |
| 5. Lubricants (Oils/silicones) | 0.5–15 |
| 6. Quaternized Hemp Seed Oil | 0.01–10 |
| 7. Fixative Polymer | 0–15 |

Preservatives, fragrance and color as necessary.

Skin Care Products

Creams and lotions provide skin emollients, moisturizers and active ingredients by way of an emulsion. The products improve the appearance and condition of the skin. They differ from each other in consistency. Creams are typically thick and non-pourable, whereas lotions are lower in viscosity.

Creams and lotions are emulsions, and can be either oil-in-water or water-in-oil systems. They are primarily comprised of emulsifiers, thickeners, stabilizers, humectants and conditioners. They contain preservatives for safety reasons and fragrances and color for aesthetic appeal. Functional ingredients such as botanicals are often incorporated in the emulsions.

Skin cells readily absorb essential fatty acids into the barrier layer of the skin. A cream or lotion rich in essential fatty acids can help replenish skin cells damaged by the environment, i.e. sun, dryness, or surfactant damage. Hemp seed oil is high in essential omega-3 and omega-6 fatty acids, such as linoleic and linolenic acids.

TABLE 7

Sample Formulation of Creams/Lotions

| Ingredient | % |
|---|---|
| Part A | |
| 1. Emulsifying Waxes (emulsifer) | 1–15 |
| 2. Oils (botanicals or silicones, etc.) | 0.5–20 |
| 3. Emollient Esters | 1–20 |
| 4. Fatty Alcohols | 0.5–20 |
| 5. Quaternized Hemp Seed Oil | 0.01–10 |
| Part B | |
| 1. Water | QS |
| 2. Thickener (Acrylic, gums, polymers) | 0.1–1 |
| 3. Humectants | 0.5–15 |
| Part C | |
| 1. Active Ingredients | 0.1–30 |

(Maya consist of sunscreens alpha or beta hydroxy acids, treatment ingredients)
Preservatives, fragrance and color as necessary In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. A method of making a cosmetic composition containing fatty acids, comprising:
   at least partially hydrolyzing hempseed oil to produce free fatty acids substantially in the absence of oxygen; and
   quaternizing the free fatty acids,
   wherein quaternizing the free fatty acids comprises reacting the free fatty acids with a tertiary amine having the formula

wherein $R_1$ and $R_2$ are each alkyl groups of one to four carbons, and $R_3$ is an aliphatic alkyl having 8 to 22 carbons.

2. The method of claim 1, further comprising incorporating the product of claim 1 in a cosmetic preparation.

3. The method of claim 2, wherein incorporating the product in a cosmetic composition comprises incorporating the quaternized free fatty acids in a shampoo, conditioner, styling product, or skin care product.

4. The method of claim 1, wherein hydrolyzing the hemp seed oil comprises saponifying the oil by heating the oil, in the presence of a sufficient amount of a catalyst selected from ZnO, MgO, CaO, LiOH, NaOH, KOH, or NH₄OH, in a nitrogen atmosphere at an elevated pressure for a sufficient period of time to substantially completely saponify the hemp seed oil while substantially avoiding cross-linking or oxidizing free fatty acid products of hydrolyzing hemp seed oil.

5. The method of claim 1, wherein $R_3$ is aliphatic alkyl having 12 to 18 carbons.

6. The method of claim 1, wherein the tertiary amine is dimethylcetylamine.

7. A method of making a cosmetic composition, comprising:
saponifying hemp seed oil, in the presence of a base, at a temperature of about 180° C. and in the substantial absence of oxygen, to produce hemp seed oil free fatty acids;
quaternizing the free fatty acids by reacting the free fatty acids with a tertiary amine.

8. The method of claim 7, further comprising incorporating the quaternized free fatty acids into a cosmetic composition.

9. A quaternized hemp seed oil composition made by the method of claim 1.

10. A cosmetic composition made by the method of claim 8.

11. Quaternized hemp seed oil, comprising a quaternary ammonium salt of free fatty acids comprising a mixture of palmitic acid, stearic acid, arachidic acid, behenic acid, palmitoleic acid, oleic acid, linoleic acid, and linolenic acid, that have been saponified and quaternized in a substantial absence of oxygen, to minimize oxidative cross-linking of the free fatty acids,
wherein quaternizing the free fatty acids comprises reacting the free fatty acids with a tertiary amine having the formula

wherein $R_1$ and $R_2$ are each alkyl groups of one to four carbons, and $R_3$ is an aliphatic alkyl having 8 to 22 carbons.

12. The quaternized hemp seed oil of claim 11, wherein the linoleic and linolenic acids comprise omega-6 linoleic acid, omega-3 linolenic acid, and omega-6 linolenic acid.

13. A method of making a cosmetic composition, comprising:
saponifying hemp seed oil, in the presence of a metallic hydroxide catalyst in an amount of about 2–4%, in a substantial absence of oxygen, under a nitrogen atmosphere at a pressure of about 150 p.s.i., at a temperature of about 180° C., to produce hempseed fatty acids; and
quaternizing the hempseed fatty acids by reacting them with dimethylcetylamine under a substantial vacuum.

14. A quaternized hempseed oil composition made by the method of claim 13.

15. The method of claim 1, wherein quaternizing the free fatty acids comprises quaternizing the free fatty acids substantially in an absence of oxygen.

16. The method of claim 7, wherein quaternizing the free fatty acids comprises quaternizing the free fatty acids substantially in an absence of oxygen.

* * * * *